United States Patent
Donker et al.

(10) Patent No.: US 10,691,990 B2
(45) Date of Patent: Jun. 23, 2020

(54) SYSTEM AND METHOD FOR CAPTURING SPATIAL AND TEMPORAL RELATIONSHIPS BETWEEN PHYSICAL CONTENT ITEMS

(71) Applicant: KONINKLIJKE PHILIPS N.V., Eindhoven (NL)

(72) Inventors: Victor Barend Hendrik Donker, Eindhoven (NL); Jori Marcellinus Nicole Verbeek, Eindhoven (NL); Johan Partomo Djajadiningrat, Utrecht (NL); Lucas Jacobus Franciscus Geurts, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/309,279

(22) PCT Filed: Jun. 7, 2017

(86) PCT No.: PCT/EP2017/063747
§ 371 (c)(1),
(2) Date: Dec. 12, 2018

(87) PCT Pub. No.: WO2017/215986
PCT Pub. Date: Dec. 21, 2017

(65) Prior Publication Data
US 2019/0325278 A1  Oct. 24, 2019

(30) Foreign Application Priority Data
Jun. 13, 2016 (EP) ..................... 16174176

(51) Int. Cl.
*G06F 17/00* (2019.01)
*G06K 19/06* (2006.01)
*G06K 19/07* (2006.01)

(52) U.S. Cl.
CPC ... *G06K 19/06009* (2013.01); *G06K 19/0723* (2013.01)

(58) Field of Classification Search
USPC ........................................................ 235/375
See application file for complete search history.

(56) References Cited

U.S. PATENT DOCUMENTS

| | | | |
|---|---|---|---|
| 2004/0205478 A1* | 10/2004 | Lin ........................ | G06F 16/40 715/202 |
| 2006/0232012 A1* | 10/2006 | Boyer ...................... | A63F 1/00 273/292 |
| 2007/0297695 A1 | 12/2007 | Aratani et al. | |
| 2008/0004902 A1 | 1/2008 | Leong-Fern et al. | |
| 2008/0033757 A1 | 2/2008 | Kozloff et al. | |

(Continued)

OTHER PUBLICATIONS

Barton et al: "The Meeting Machine: Interactive Workspace Support for Nomadic Users"; Proceedings of the Fifth IEEE Workshop on Mobile Computing Systems & Applications (WMCSA 2003), 2003 IEEE pp. 1-11.

(Continued)

*Primary Examiner* — Tuyen K Vo

(57) ABSTRACT

The present invention relates to a system (1) for capturing spatial and temporal relationships between physical content items (2) and user actions related to the physical content items (2), comprising a sensor unit (3) for detecting the physical content items (2) and for outputting sensor data, a monitoring device (4) for user identification and monitoring of user action related to the physical content items (2) and for outputting monitoring data, and a processor (5) for processing said sensor data and said monitoring data by prioritizing and interrelating said sensor data and said monitoring data in correspondence to the frequency and/or duration of the at least one user action in connection with the at least one physical content items (2) and for generating a data set including said prioritized and interrelated sensor data and monitoring data.

16 Claims, 2 Drawing Sheets

(56) References Cited

U.S. PATENT DOCUMENTS

| | | | |
|---|---|---|---|
| 2009/0062003 A1* | 3/2009 | Kerscher | A63F 1/18 |
| | | | 463/36 |
| 2009/0174670 A1 | 7/2009 | Diederiks | |
| 2011/0063440 A1* | 3/2011 | Neustaedter | H04N 5/144 |
| | | | 348/143 |
| 2011/0130184 A1* | 6/2011 | Mills | A63F 1/00 |
| | | | 463/13 |
| 2012/0081551 A1 | 4/2012 | Mizuno et al. | |
| 2013/0218137 A1* | 8/2013 | Abovitz | A61B 90/98 |
| | | | 606/1 |

OTHER PUBLICATIONS

Bianchi et al:"MagniID: Tracking Multiple Magnetic Tokens"; YouTube, Abstract, Recorded at the 9th Intl Conference on Tangible, Embedded and Embodied Interaction, Stanford, CA Jan. 15-19, 2015, Published on April 7, 2016.

Jacob et al: "A Tangible Interface for Organizing Information Using a Grid"; Proceedings of CHI 2002, ACM Press, pp. 1-8.

Jaimes et al: Building a Smart Meeting Room: From Infrastructure to the Video Gap (Research and Open Issues), Proceedings of the 21st International Conference on Data Engineering (ICDE '05), pp. 1-10.

Kane et al: "Bonfire: A Nomadic System for Hybrid Laptop-Tabletop Interaction"; Proceedings of the 22nd Annual ACM Symposium on User Interface Software and Technology, UIST '09, Jan. 2009. New York, New York, pp. 129-138.

Rekimoto et al: "DataTiles: A Modular Platform for Mixed Physical and Graphical Interactions"; CHI 2001, Mar. 31-Apr. 5, 2001, Seattle, WA, pp. 269-276.

Weibel et al: "Lab-In-A-Box: Semi-Automatic Tracking of Activity in the Medical Office"; Pers Ubiquit Comput (2015), 19:317-334.

\* cited by examiner

SYSTEM AND METHOD FOR CAPTURING SPATIAL AND TEMPORAL RELATIONSHIPS BETWEEN PHYSICAL CONTENT ITEMS

CROSS-REFERENCE TO PRIOR APPLICATIONS

This application is the U.S. National Phase application under 35 U.S.C. § 371 of International Application No. PCT/EP2017/063747, filed on Jun. 7, 2017, which claims the benefit of European Patent Application No. 16174176.4, filed on Jun. 13, 2016. These applications are hereby incorporated by reference in their entirety herein.

FIELD OF THE INVENTION

The present invention relates to a system, apparatus and a method for capturing information relating to the handling time and frequency and other spatial and temporal information connected to a physical content item during a session, especially a medical consultation or the like.

BACKGROUND OF THE INVENTION

It is known that a person provided with information during a communication will only remember a small part of what has been communicated if speech is the only form of presentation. It is therefore desirable to choose other forms of presenting information to enhance the contingent of data remembered. Nowadays, it is common practice to add visual, audio and other parts of information to support reception of data. If a person who has previously been presented with information during a communication like a consultation at a medical practitioner tries to recap the information content of the consultation, the person will be more successful if any form of information provided, like speech, images, audio data, etc., are available.

US 2012/0081551 A1 discloses a monitoring system for a work area by use of a camera. The system includes three locations of work areas each connected to a network, image-sound analyzing means, image-sound storing means, data managing means, a system control center, and a browser terminal. A part relating to image-capture and sound pickup inside the work area includes a WEB camera, a microphone fixed to the WEB camera, an image-capture range, a marking indicating plate placed in the image-capture range, two stripe markings put on the surface of the marking indicating plate, and a two-dimensional bar-code put together with the stripe markings.

The monitoring system disclosed in the aforementioned document only monitors the action taking place in the monitored work area without collection additional information interrelating the observed activities. The information content of the data set thus is incomplete and leaves a user who looks at a playback of the data set in doubt about connections and importance of the activities.

SUMMARY OF THE INVENTION

It is an object of the present invention to provide a monitoring system, apparatus and method, which not only monitor activity, but connect the data collected during a session and thus enhance the contents of the data set for the users' convenience and support the information directly conveyed during the session by additional content.

In a first aspect of the present invention a system for capturing spatial and temporal relationships between at least one physical content item and at least one user action related to the at least one physical content item is presented, the system comprising
a sensor unit for detecting the at least one physical content item and for outputting sensor data,
a monitoring device for monitoring the at least one user action related to the at least one physical content item and for outputting monitoring data, and
a processor for processing said sensor data and said monitoring data by prioritizing and interrelating said sensor data and said monitoring data in correspondence to the frequency and/or duration of the at least one user action in connection with the at least one physical content items and for generating a data set including said prioritized and interrelated sensor data and monitoring data.

In a second aspect of the present invention an apparatus for capturing a spatial and temporal relationships between at least one physical content item and at least one user action related to the at least one physical content item, the apparatus comprising:
a first input unit for receiving sensor data from a sensor unit (3), said sensor data indicative of a detection of the at least one physical content item (2),
a second input unit for receiving monitoring data from a monitoring device (4), said monitoring data indicative of the at least one user action in relation to the at least one physical content item (2), and
a processor (5) for processing said sensor data and said monitoring data by prioritizing and interrelating said sensor data and said monitoring data in correspondence to the frequency and/or duration of the at least one user action in connection with the at least one physical content items (2) and for generating a data set including said prioritized and interrelated sensor data and monitoring data.

In a further aspect of the present invention a method for capturing spatial and temporal relationships between at least one physical content item and at least one user action related to the at least one physical content item is presented, comprising the steps of
receiving sensor data from a sensor unit regarding placing of the at least one physical content item on the sensor unit,
receiving monitoring data from a monitoring device monitoring at least one user action related to the at least one physical content item,
processing said sensor data and said monitoring data by prioritizing and interrelating said sensor data and said monitoring data in correspondence to the frequency and/or duration of the at least one user action in connection with the at least one physical content item, and
generating a data set including said prioritized and interrelated sensor data and monitoring data.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as defined in the dependent claims and as disclosed herein.

In an embodiment, a computer system or device may be provided which comprises: a computer program product according to an embodiment; and one or more processors adapted to perform a method according to an embodiment by execution of the computer-readable program code of said computer program product. The system or device can comprise a client device and server device, or either one of the two for execution of the method steps. The server and client device can have communication devices for communicating with each other using wired or wireless communication protocols.

In a further aspect the invention relates to a computer-readable non-transitory storage medium comprising instructions which, when executed by a processing device, execute the steps of the method for capturing spatial and temporal relationships between at least one physical content item and at least one user action related to the at least one physical content item.

The computer program product can have code for communicating results of any of the method steps to a user. Such code can include code for generating imagery, video and/or audio output. The system, client and/or server device can include a display and/or audio output devices (such as speakers) for generating the output.

Since it is well known that only a small amount of verbally conveyed information will be remembered over a longer time, it is crucial for e.g. a patient being prepared for surgery to have other sources of information to recall the consultation correctly. The proposed system not only collects information related to physical content items during a consultation, but connects the monitored activities to each other, thus supplementing the information content beyond the topics discussed during the consultation. By way of connecting spatial and temporal information, a prioritization of the discussed topics can be achieved. Optional identification of the participants further helps to complete the information spectrum beyond a short consultation, as does additional media content or information from expert databases.

According to preferred embodiments of the invention, the sensor unit is part of a piece of furniture equipped with at least one sensor and/or a predefined sensor area of the piece of furniture covered by the at least one sensor, wherein the sensor area is arranged on and/or is part of the piece of furniture, and/or wherein the sensor unit is a place mat equipped with sensors. The different possibilities of arrangement of the sensor unit as part of present furniture offers a wide variety of locations where the system can be used, e.g. in the consulting room of the medical staff, in a neutral room, in the clinic room the patient is situated in or in any other chosen environment. This makes the system highly flexible and easy to transport.

According to an advantageous embodiment, the sensor unit contains a detection device (or one or more detections devices) for detection of the placement of the at least one physical content item with regard to the position and/or the proximity to one or more previously placed physical content items, with regard to the orientation, the placement order and/or the arrangement of the at least one physical content item, and/or with regard to the identification of the content of the at least one physical content item. By way of this, the physical content items can be controlled easily, and the detection data can be collected for further processing.

Preferably the physical content items contain the detection device(s) for detection of the placement of the at least one physical content item by the sensor unit. This makes handling and use very easy.

Advantageously, each of the detection device(s) can comprise one or more of a NFC tag, a RFID tag, a QR code, a bar code, and a respective sensor. The detection device(s) mentioned before are small, low cost and reliable and thus can be implemented in nearly any physical content items.

According to preferred embodiments, the monitoring device is configured to identify a user and comprises one or more of a camera, a microphone, a microphone array, a movement detector, a user identification device, a clock. Combinations of the devices are possible and contribute to a complete and reliable collection of data to keep the user fully informed about the chosen topics.

Preferably, the system further comprises a receiver for receiving sensor data from the sensor unit, data from the at least one physical content item and monitoring data from the monitoring device. Since nowadays electronic components for those purposes are small, all components can be accommodated in a housing and arranged flexibly for use in an arbitrary environment.

According to an advantageous embodiment of the invention, the system further comprises a communication unit for communication with an expert database. Communication with an expert database allows completing the dialogue of the patient and the medical staff by information being not explicitly conveyed or being optional for the consultation.

Further, the system can comprise a display unit and/or a mobile unit for displaying the sensor data from the sensor unit, data from the at least one physical content item, the monitoring data from the monitoring device, the data set generated by the processor and/or data from further sources. Computer or laptop displays thus can advantageously be used without the need of further devices. Alternatively or additionally, mobile devices like laptops, tablets or mobile phones can be used to display the data set and/or the single data.

According to a preferred embodiment of the method, placing the at least one physical content item on the sensor unit comprises identifying the at least one physical content item with respect to their content, handling time, handling frequency, position, orientation and proximity to at least one or more previously placed physical content items, and transmitting the data to the processor. By this the complete information content of the content items can be collected, thus contributing to an informative data set.

Advantageously, monitoring user action comprises identification of a user, recording of movement of a user in correspondence to the handling of at least one physical content item, recording of speech of a user in correspondence to the handling of at least one physical content item, recording of handling time and handling duration, identifying a speaker, and/or transmitting the data to the processor. The identification of the respective user (patient or medical staff) and the simultaneous recording of the content item related values as well as the communication associated with the content items help to prioritize the information with respect to later playback of the data set to the user and support the capacity of remembering of the users.

Preferably, processing the data comprises interrelating the data in spatial and temporal relationship to the at least one user action, prioritizing the data according to the spatial and temporal relationship and generating a data set providing a digital image file of the relationship of the data. By interrelation of the data with respect to time and placement context information, the user can be supported during later playback to remember the information. By prioritization of the data, the user will get the most important information first.

Processing of the data can advantageously further comprise interrelating the sensor data received from the sensor area and the monitoring data from the monitoring device with related data contained in and received from an expert data base and/or with media content being presented in succession of placement of at least one physical content item. By way of this, information can be added to the data set which is optional or has not been accounted for during the consultation. Nowadays, time is scarce and leads to short consultations often leaving many questions open or topics unattended. This can be overcome by connection of different sources of information to the consultation data set.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
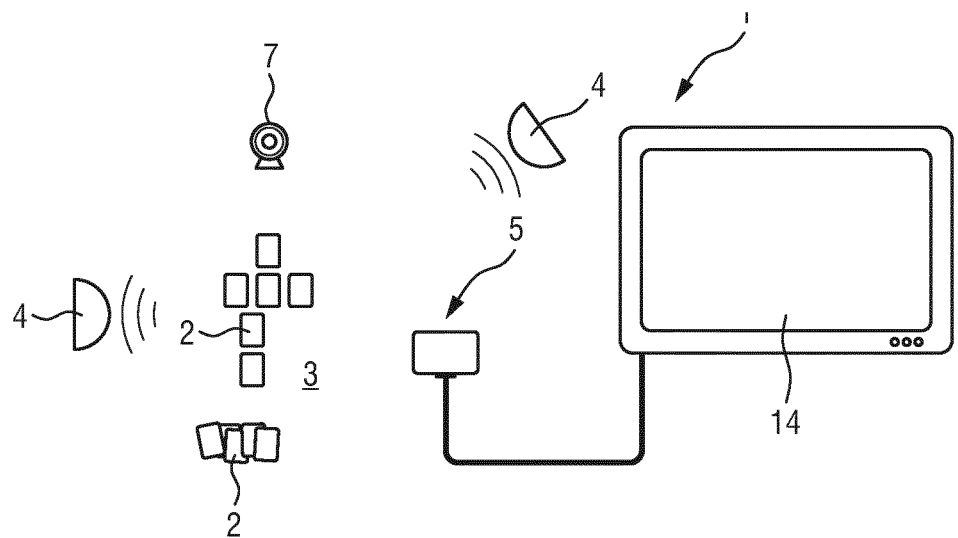
FIG. 1 shows a schematic diagram of a first embodiment of a system according to the present invention.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

The present invention starts from the goal to enhance the communication between a patient and medical staff, e.g. a physician. As an example for application, the mamma outpatient clinic can be cited, where women with breast cancer are informed about their disease and the respective treatment plans, but are not supposed to stay long-term and will not be present in the clinic between consultation and surgery. Thus, the patient cannot receive medical information on a daily basis. Studies however showed that patients only remember about twenty percent of the verbally transferred information. Therefore, it is desirable to support the verbally transferred information by visualized contents and possible additional other contents like media or data from an expert database and to capture the information in a tangible embodiment to enhance the amount of remembered information by enhanced consistency and continuity of the information.

Generally, the present invention proposes to store information that is presented tangibly and visually during the consult and to prepare a data set which can be recalled in exactly the same visual layout in the digital environment at home. This is achieved by capturing the spatial and temporal relations between the audio, visual and other contents and translating this to a virtual content which can be reproduced later. This may also include verbal information uttered by the medical staff and/or questions and comments of the patient being recorded during handling of content items or media. The possibility to recall the information gives the patient a feeling of better control of the disease and the respective treatment and thus helps to enhance the success of the therapy. Furthermore, the information can be prioritized due to the values of handling time and duration of content items containing the respective information. The prioritization then leads to a respective arrangement of the information in the data set. The user will be presented during playback with the prioritized information first, which arises from the own prioritization during consultation by often/long handling of the respective physical content items.

FIG. 1 shows a schematic diagram of a first embodiment of a system according to the present invention. The disclosed system 1 comprises at least one physical content item 2 which for example can take the form of cards, tokens, pads, plates or the like. A physical content item 2 is defined as a physical object which can be picked up, handled and placed by the patient and/or medical staff and which at least contains a subject related content like a diagnosis or parts thereof, symptoms, surgical methods or conservative treatments to be proposed to the patient, medication, risks, chances and other topics in connections to the disease or medical topic discussed. In addition to the above aspect describing that the subject of the physical content item 2 can relate to or represent a diagnosis or parts thereof etc., the physical content items 2 are identified by certain technical features, which can for example comprise or include QR— or bar code(s), detectable pictures or pictogram(s), RFID/NFC identification chip(s)/tag(s), or any other sensor or means able to track and/or identify the physical content items 2. The identification can then comprise detection of the physical content items 2 by corresponding sensors like image cameras, RFID readers etc.

Preferably, a multitude of physical content items 2 is present. The physical content items 2 are handled and placed by the patient and/or by the medical staff during communication. Handling and placement are surveyed by sensors 7, in FIG. 1, by a camera which is arranged to survey a certain area e.g. on a table. The area surveyed by the camera is generally called a sensor unit 3 which can contain integrated sensors 7, remote sensors 7 like the camera or a combination thereof. Different embodiments of the sensor unit 3 might contain arbitrary surfaces of furniture, e.g. a table, or a bedside cabinet in a clinics room. Alternatively, a portable mattress for arbitrary positioning can be provided, for example when the patient has to stay in bed during the consultation.

As can be seen in FIG. 1, several physical content items 2 have already been placed in the area of the sensor unit 3, some more have not been used and are stacked next to the sensor unit 3. The physical content items 2 which have already been placed show an arbitrary arrangement reflecting the relationship of the physical content items 2 to each other and the importance assigned to them by the user, e.g. by placing them close to each other, handling them longer or more often than other physical content items 2 and so on. The spatial and temporary arrangement of the physical content items 2 is surveyed by the camera and transmitted to a processor 5 for being processed, associated with additional information and stored. The additional information can e.g. be the communication taking place between the patient and the medical staff during handling and placement which is recorded by monitoring devices 4 like a microphone or an array of microphones and/or at least one camera. Further monitoring devices like clocks, timer, vital signs monitoring devices and the like can be provided where appropriate. Vital signs monitoring can e.g. be used to monitor pulse, blood pressure or conductivity of skin to capture stress, anxiety or other emotional reactions related with the content of the physical content items 2. Besides, further information like media contents activated by pick-up, handling or placement of the physical content items 2, information derived from an expert data base depending on the content of the physical content items 2 handled and other sources of information can be recorded and included in the data. By way of the microphone/microphone array and/or the camera, an identification of the speaker can take place to correctly associate the handling of the physical content items 2 to the respective handling person.

Figure 3:
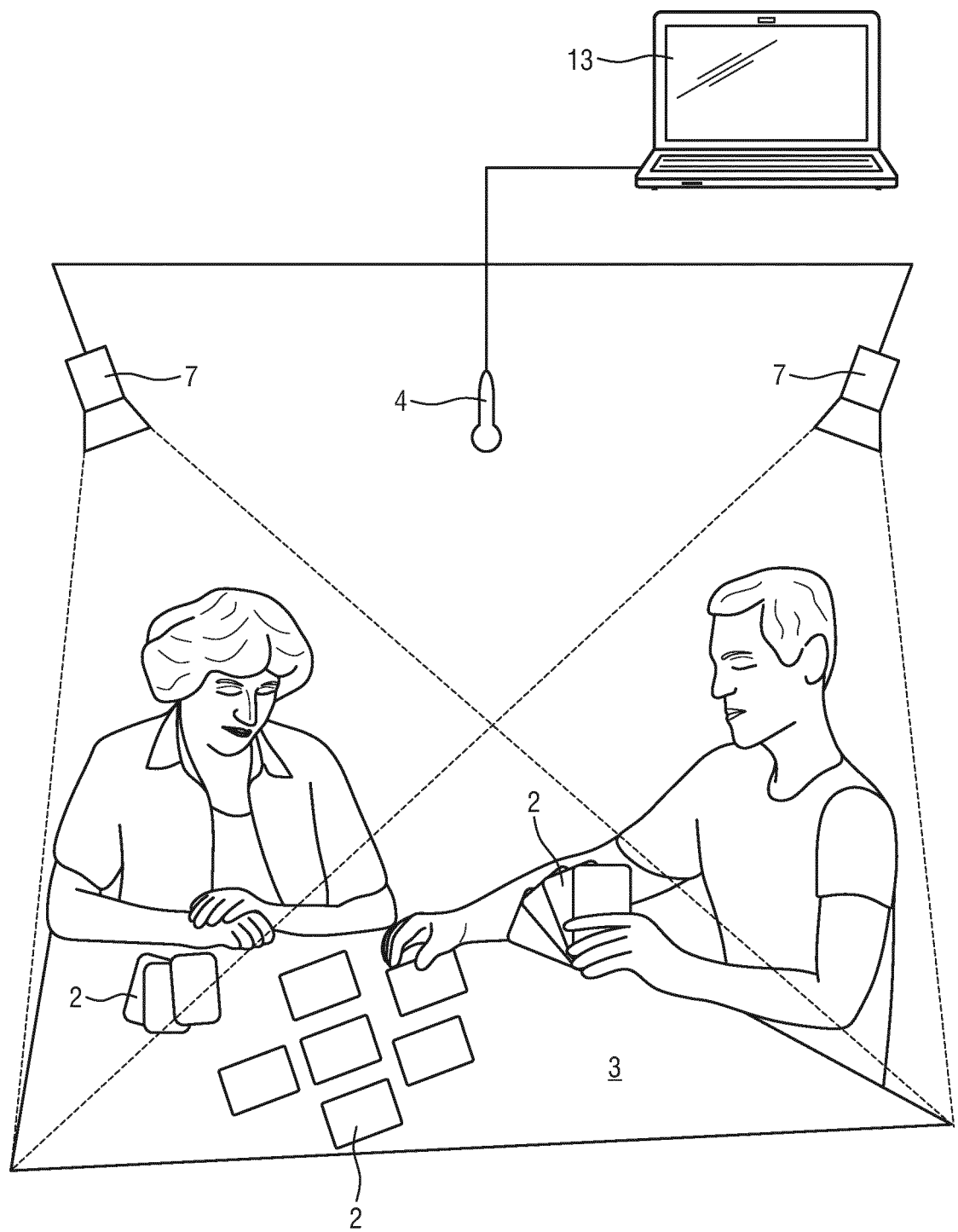
FIG. 3 shows an illustrative example of a consultation assisted by a system according to the present invention.

In FIG. 3, a consultation between a medical staff person and a patient is schematically shown. The persons involved handle the physical content items 2, discuss them and position them while monitoring devices 4, in this case two cameras 7 and a microphone 4, record the consultation. A computer 13 collects the data for later processing and recording.

Any activity of the persons involved in the communication is gathered by the different components of the system 1 and transmitted e.g. wireless to the processor 5. This includes e.g. information about who was talking, which physical content items 2 were picked up, handled and placed during speech, where and in which relation to the other physical content items 2 has the content item 2 actually handled been placed, where was the physical content item 2 removed from (from the sensor unit 3 where it had been placed previously or from the stack of content items 2 not used until this time), which additional information was presented, in which order the content items 2 have been placed, whether a certain layout can be identified, etc. As soon as the consultation has ended and the complete data have been gathered, the different parts of information are associated to each other with respect to their relation occurring during communication. The placement of the physical content items 2 is recorded with respect to the frequency and/or duration of handling, further taking into account the position of the physical content items 2 with respect to each other, the orientation of the physical content items 2, the proximity/distance of the single physical content items 2, the order of placement, the person who handled/placed the physical content items 2 and the content of the physical content items 2 itself. A time stamp can be assigned to each handling of a physical content item 2 to allocate a time line to the communication.

It is also possible to assign actions to physical content items 2. If for example the medical staff picks up a physical content item 2 and gives a voice command or presses a button, media content can be presented to the patient with respect to the chosen physical content item 2. This action and the information presented thereafter are also recorded and stored.

Later on, an analysis of the different components of the data is possible. For example, the duration and/or frequency of handling of the physical content items 2 can be used to prioritize the content of the physical content items 2. Physical content items 2 handled longer and/or more frequently are thus recognized to have a high priority either to the patient or to the medical staff. If for example the patient often picks up and replaces the physical content item 2 with content relating to surgery, the patient may be emotionally concerned about this topic. Further prioritization can also be achieved by analysis of the emotions of the patient handling the content items 2 by way of speech analysis via a microphone, a mimic analysis via a camera or measurement of certain vital signs like pulse, blood pressure or the like by vital signs monitoring devices. Besides, the hierarchy of the placement can be used to determine the importance of contents for the patient which can also be used to prioritize the data for the convenience of the patient. This in turn can trigger more information about the surgery to be provided—e.g. from the expert data base and help the medical staff to provide further help on this topic. The additional helpful information will be stored alongside the data about handling frequency and duration and might be used to highlight the respective physical content item 2 in the data set to be generated. During playback, these contents might be presented first to the user or highlighted to show their priority.

During the consultation it is further possible to set bookmarks for designated layouts of the physical content items 2, e.g. to show alternative treatment plans. The patient then can later recall different discussed options easily, e.g. when a decision between two options for treatment of a disease has to be made one of which might suggest surgery, whereas the other possibility might suggest a conservative approach.

If the communication is over and the information is complete, the data set will be generated by the processor 5. The data set is a compilation of all information gathered during the consultation and stored in exactly the context in which any information was presented. Thus, a timeline will be generated helping the user during playback to retrace the order of the different bits of information with respect to the physical content items 2, recognize topics with high priority and remember the information connected therewith. The digital file generated by the processor is a kind of virtual environment indicative of the reality and can be saved for future use for the patient as well as for the medical staff. The patient can recall the consultation and the treatment presented therein at home to get accustomed to the different aspects, and the medical staff can recall the communication to selectively prepare for questions which might for example arise from prioritized physical content items 2 at the patient's end.

Figure 2:
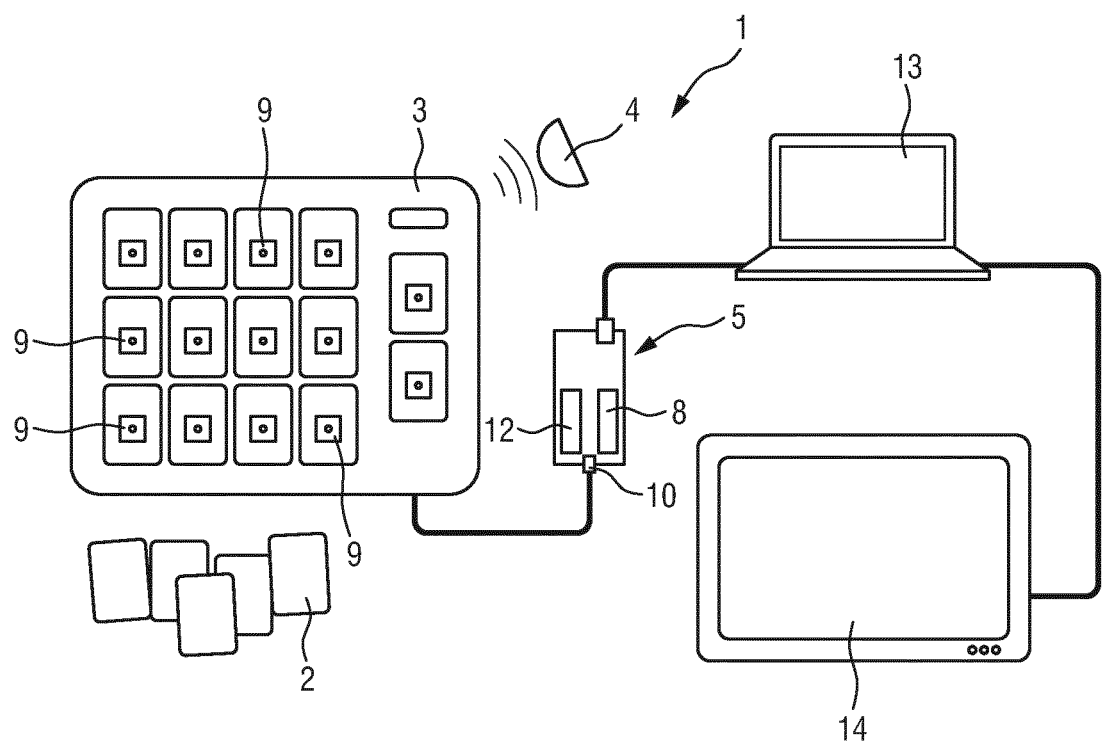
FIG. 2 shows a schematic diagram of a second embodiment of a system according to the present invention.

The digital file can for example be stored in a storage 8 as shown in FIG. 2 and distributed therefrom, or it can be stored on a portable medium or in a cloud. The user can reproduce and view the digital file on a mobile unit 14 like a tablet or a mobile phone, or on a personal computer.

While in FIG. 1 the detection of the physical content items 2 takes place by way of the camera, there are other possibilities to detect the position and the handling frequency and duration of the physical content items 2. FIG. 2 shows a schematic diagram of a second embodiment of a system according to the present invention, particularly illustrating another possibility of detection. Components that are identical to FIG. 1 have been referenced with the same reference signs.

In FIG. 2, the sensor unit 3 has a predetermined shape and size resembling a place mat and containing a grid for arrangement of the physical content items 2. An advantage of this embodiment is the possibility to use the system without a table, when e.g. the patient has to stay in bed.

Detection of the physical content items 2 is in this case achieved by the presence of detection devices 9 arranged in the grid of the sensor unit 3. The detection devices 9 can for example be RFID chips, NFC devices, or any sort of optical code like a QR code or a bar code. Further, the detection devices 9 can be arranged in the sensor unit 3 and/or in the physical content items 2. A possible non-limiting combination would for example be RFID chips in the physical content items 2 communicating with NFC devices embedded in the sensor unit 3 or vice versa. Reference is made in this regard to the commonly known technique of body couple communication to detect which of the physical content items 2 has been touched or moved and by whom. Arrays of RFID readers in the sensor unit 3 can be used to identify a position of a physical content item 2 carrying an RFID tag by way of measuring the signal strength in any of the RFID readers.

The camera of FIG. 1 can also be used to detect codes on the physical content items 2, for example QR-codes, and thus detect the position/orientation of the physical content items 2 as well as the content itself.

As in the preceding embodiment, the participants of the consultation can take, handle, place and replace the physical content items 2 and discuss the content thereof. The physical content items 2 however now can only be placed in the respective places within the grid on the sensor unit 3. The detection devices 9 will again communicate the time-stamp, handling duration/frequency and potential connected information like media to the processor 5 for further processing and compilation.

The processor 5 is in this embodiment connected to the sensor unit 3 and receives the signals thereof. A receiver 10 can also be provided to further receive signals from the monitoring device(s) 4. A communication unit 12 can be provided for communication with an expert data base, a cloud storage or other storage devices e.g. to load media content in connection with the physical content items 2 placed. A display unit 13 like a computer, a monitor or the like can be used during the consultation to present the data collected during the communication in connection with the actions regarding the physical content items 2. Again, a mobile device 14 can be used by the participants of the consultation to recall the information via the digital data file generated by the processor 5 and stored e.g. in the storage 8 or on any other suitable medium or location like a cloud.

In an alternative embodiment (not shown), the processor may be incorporated in a standalone apparatus or product, and comprises input units, a first input unit and a second input unit, for respectively receiving sensor data from the sensor unit 3, said sensor data indicative of a detection of the at least one physical content item 2, and monitoring data from the monitoring device 4, said monitoring data indicative of the at least one user action in relation to the at least one physical content item 2). This embodiment is advantageous in that it enables an everyday life device, such as a mobile phone, a computer, a tablet or any other portable device that can be handled or carried by a user in receiving data of the kind herein mentioned from a network, or alternatively from Wi-Fi, or Bluetooth or any other wireless means, such that the processor (for instance a processing unit, a chip) imbedded or coupled to this device processes said sensor data and said monitoring data by prioritizing and interrelating said sensor data and said monitoring data in correspondence to the frequency and/or duration of the at least one user action in connection with the at least one physical content items and for generating a data set including said prioritized and interrelated sensor data and monitoring data.

The skilled in the art will understand that processing unit of the apparatus according to the present invention comprises similar advantages and effects as the processing unit of the system according the present invention, and all information mentioned herein relative to the processing unit of the system according the present invention applies to the processor of the apparatus according to the present invention.

While the application of the invention has been described with respect to the healthcare section, also other fields of application are possible. A use of this concept for education, especially for early stage learning, might be considered. Besides, the use in a business environment to explain processes is possible.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for capturing spatial and temporal relationships between at least one physical content item and at least one user action related to the at least one physical content item, the system comprising:
   a sensor unit for detecting the at least one physical content item and for outputting sensor data,
   a monitoring device for monitoring the at least one user action related to the at least one physical content item and for outputting monitoring data, and
   a processor for processing said sensor data and said monitoring data by prioritizing and interrelating said sensor data and said monitoring data in correspondence to the frequency and/or duration of the at least one user action in connection with the at least one physical content item, and for generating a data set including said prioritized and interrelated sensor data and monitoring data,
   wherein the processor is configured to process said sensor data and said monitoring data such that said sensor data and said monitoring data has a first temporal order, and
   wherein the processor is configured to generate a review of said sensor data and said monitoring data for display to the user, said review determined based on said prioritizing and the interrelating, said review comprising the sensor data and the monitoring data arranged in a prioritized, second temporal order that is different than the first temporal order.

2. The system according to claim 1, wherein the sensor unit is integrally formed in a piece of furniture equipped with at least one sensor of the sensor unit, or wherein the sensor unit is a place mat equipped with at least one sensor.

3. The system according to claim 1, wherein the sensor unit comprises a detection device for detection of the placement of the at least one physical content item:
with regard to the position, and/or the proximity to one or more previously placed physical content items; and/or
with regard to the orientation, the placement order and/or the arrangement of the at least one physical content item.

4. The system according to claim 1, wherein the at least one physical content item comprises a detection device for detection of the placement of the at least one physical content item by the sensor unit.

5. The system according to claim 3, wherein the detection device comprises one or more of a NFC tag, a RFID tag, a QR code, a bar code, and a respective sensor.

6. The system according to claim 1, wherein the monitoring device is configured to identify a user and/or comprises one or more of at least one camera, a microphone, a microphone array, a movement detector, a user identification device, or a clock.

7. The system according to claim 1, further comprising a receiver for receiving sensor data from the sensor unit, data from the at least one physical content item and monitoring data from the monitoring device.

8. The system according to claim 1, further comprising a communication unit for communication with an expert database.

9. The system according to claim 1, the system further comprising a display unit and/or a mobile unit for displaying the sensor data from the sensor unit, data from the at least one physical content item, the monitoring data from the monitoring device, and/or the data set generated by the processor.

10. An apparatus for determining spatial and temporal relationships between at least one physical content item and at least one user action related to the at least one physical content item, the apparatus comprising:
a first input unit for receiving sensor data from a sensor unit, said sensor data indicative of a detection of the at least one physical content item,
a second input unit for receiving monitoring data from a monitoring device, said monitoring data indicative of the at least one user action in relation to the at least one physical content item, and
a processor for processing said sensor data and said monitoring data by prioritizing and interrelating said sensor data and said monitoring data in correspondence to the frequency and/or duration of the at least one user action in connection with the at least one physical content items, and for generating a data set including said prioritized and interrelated sensor data and monitoring data,
wherein the processor is configured to process said sensor data and said monitoring data such that said sensor data and said monitoring data has a first temporal order, and
wherein the processor is configured such that the data set is arranged in a prioritized, second temporal order that is different than the first temporal order.

11. A method for capturing spatial and temporal relationships between at least one physical content item and at least one user action related to the at least one physical content item, comprising:
receiving sensor data from a sensor unit regarding placing of the at least one physical content item on the sensor unit,
receiving monitoring data from a monitoring device monitoring at least one user action related to the at least one physical content item,
processing said sensor data and said monitoring data by prioritizing and interrelating said sensor data and said monitoring data in correspondence to the frequency and/or duration of the at least one user action in connection with the at least one physical content item, and
generating a data set including said prioritized and interrelated sensor data and monitoring data,
wherein said sensor data and said monitoring data has a first temporal order, and
wherein said data set is configured such that the sensor data and the monitoring data are arranged in a prioritized, second temporal order that is different than the first temporal order.

12. The method according to claim 11, wherein placing the at least one physical content item on the sensor unit comprises identifying the at least one physical content item with respect to their content, handling time, handling frequency, position, orientation and proximity to at least one or more previously placed physical content item, and transmitting the data to the processor.

13. The method according to claim 11, wherein monitoring at least one user action comprises:
identification of a user,
recording of movement of a user in correspondence to the handling of at least one physical content item,
recording of speech of a user in correspondence to the handling of at least one physical content item,
recording of handling time and handling duration,
identifying a speaker, and/or
transmitting the data to the processor.

14. The method according to claim 11, wherein processing the data comprises interrelating the data in spatial and temporal relationship to the at least one user action, prioritizing the data according to the spatial and temporal relationship and generating a data set providing an digital image file of the relationship of the data.

15. The method according to claim 14, wherein processing the data further comprises interrelating the sensor data received from the sensor unit and the monitoring data received from the monitoring device with related data contained in and received from an expert data base and/or with media content being presented in succession of placement of at least one physical content item.

16. A computer program product for capturing spatial and temporal relationships between at least one physical content item and at least one user action related to the at least one physical content item, the computer program product comprising computer-readable program code downloadable from a communications network, or storable on, or stored on a computer-readable storage medium, which computer-readable program code, when run on a computer causes the computer to perform the steps of claim 11.

* * * * *